(12) United States Patent
Brannan

(10) Patent No.: US 8,764,744 B2
(45) Date of Patent: Jul. 1, 2014

(54) SYSTEM FOR MONITORING ABLATION SIZE

(75) Inventor: Joseph D. Brannan, Erie, CO (US)

(73) Assignee: Covidien LP, Mansfield, MA (US)

( * ) Notice: Subject to any disclaimer, the term of this patent is extended or adjusted under 35 U.S.C. 154(b) by 854 days.

(21) Appl. No.: 12/692,856

(22) Filed: Jan. 25, 2010

(65) Prior Publication Data

US 2011/0184403 A1   Jul. 28, 2011

(51) Int. Cl.
*A61B 18/18* (2006.01)

(52) U.S. Cl.
USPC .............................. 606/41; 606/50; 607/101

(58) Field of Classification Search
USPC ................ 606/41–52, 33; 607/101, 104, 105, 607/154–156
See application file for complete search history.

(56) References Cited

U.S. PATENT DOCUMENTS

| | | | |
|---|---|---|---|
| D263,020 S | 2/1982 | Rau, III | |
| D295,893 S | 5/1988 | Sharkany et al. | |
| D295,894 S | 5/1988 | Sharkany et al. | |
| 5,383,917 A | 1/1995 | Desai et al. | |
| 5,398,683 A * | 3/1995 | Edwards et al. | 600/374 |
| 5,405,346 A | 4/1995 | Grundy et al. | |
| 5,800,484 A * | 9/1998 | Gough et al. | 607/104 |
| D424,694 S | 5/2000 | Tetzlaff et al. | |
| D425,201 S | 5/2000 | Tetzlaff et al. | |
| 6,241,725 B1 | 6/2001 | Cosman | |
| D449,886 S | 10/2001 | Tetzlaff et al. | |
| D457,958 S | 5/2002 | Dycus et al. | |
| D457,959 S | 5/2002 | Tetzlaff et al. | |
| 6,391,024 B1 | 5/2002 | Sun et al. | |
| 6,478,793 B1 | 11/2002 | Cosman et al. | |
| 6,506,189 B1 | 1/2003 | Rittman, III et al. | |
| 6,530,922 B2 | 3/2003 | Cosman et al. | |
| 6,575,969 B1 * | 6/2003 | Rittman et al. | 606/41 |
| 6,622,731 B2 | 9/2003 | Daniel et al. | |
| D496,997 S | 10/2004 | Dycus et al. | |
| D499,181 S | 11/2004 | Dycus et al. | |
| 6,881,214 B2 | 4/2005 | Cosman et al. | |
| D525,361 S | 7/2006 | Hushka | |
| 7,108,696 B2 | 9/2006 | Daniel et al. | |

(Continued)

FOREIGN PATENT DOCUMENTS

| | | |
|---|---|---|
| DE | 390937 | 3/1924 |
| DE | 1099658 | 2/1961 |

(Continued)

OTHER PUBLICATIONS

European Search Report for European Application No: 11000548 dated Apr. 14, 2011.

(Continued)

*Primary Examiner* — Linda Dvorak
*Assistant Examiner* — Jocelyn D Ram

(57) ABSTRACT

A system for monitoring ablation size is provided. The system includes a power source including a microprocessor for executing one or more control algorithms. A microwave antenna is configured to deliver microwave energy from the power source to tissue to form an ablation zone. A plurality of spaced-apart electrodes is operably disposed along a length of the microwave antenna. The plurality of spaced-apart electrodes is disposed in electrical communication with one another and each of the plurality of spaced-apart electrodes has a threshold impedance associated therewith corresponding to the radius of the ablation zone.

15 Claims, 10 Drawing Sheets

(56) References Cited

U.S. PATENT DOCUMENTS

| | | | |
|---|---|---|---|
| D531,311 S | 10/2006 | Guerra et al. | |
| D533,942 S | 12/2006 | Kerr et al. | |
| D535,027 S | 1/2007 | James et al. | |
| D541,418 S | 4/2007 | Schechter et al. | |
| D541,938 S | 5/2007 | Kerr et al | |
| 7,223,264 B2 | 5/2007 | Daniel et al. | |
| 7,282,049 B2 | 10/2007 | Orszulak et al. | |
| D564,662 S | 3/2008 | Moses et al. | |
| 7,344,533 B2 | 3/2008 | Pearson et al. | |
| 7,480,533 B2 | 1/2009 | Cosman et al. | |
| 7,553,309 B2 | 6/2009 | Buysse et al. | |
| 2002/0169445 A1* | 11/2002 | Jain et al. | 606/41 |
| 2006/0079885 A1 | 4/2006 | Rick et al. | |
| 2006/0079887 A1 | 4/2006 | Buysse et al. | |
| 2008/0021448 A1 | 1/2008 | Orszulak et al. | |
| 2008/0287944 A1* | 11/2008 | Pearson et al. | 606/41 |
| 2009/0054891 A1 | 2/2009 | Buysse et al. | |
| 2010/0057074 A1* | 3/2010 | Roman et al. | 606/33 |
| 2011/0098697 A1* | 4/2011 | Brannan | 606/33 |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10328514 | 3/2005 |
| DE | 102004022206 | 12/2005 |
| DE | 202005015147 | 3/2006 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 0 882 955 | 12/1998 |
| EP | 1 159 926 | 5/2001 |
| EP | 1 645 234 | 4/2006 |
| EP | 1 645 235 | 4/2006 |
| FR | 179 607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001037775 | 2/2001 |
| JP | 2001037776 | 2/2001 |
| JP | 2001128990 | 5/2001 |
| JP | 2008142467 | 6/2008 |
| SU | 166452 | 11/1964 |
| SU | 401367 | 11/1974 |
| SU | 727201 | 4/1980 |
| WO | WO 96/34571 | 11/1996 |
| WO | WO 99/04710 | 2/1999 |
| WO | WO 9956644 | 11/1999 |

OTHER PUBLICATIONS

U.S. Appl. No. 08/483,742, filed Jun. 7, 1995.
U.S. Appl. No. 08/136,098, filed Oct. 14, 1993.
U.S. Appl. No. 12/199,935, filed Aug. 28, 2008.
U.S. Appl. No. 12/203,474, filed Sep. 3, 2008.
U.S. Appl. No. 12/236,686, filed Sep. 24, 2008.
U.S. Appl. No. 12/244,850, filed Oct. 3, 2008.
U.S. Appl. No. 12/250,110, filed Oct. 13, 2008.
U.S. Appl. No. 12/250,171, filed Oct. 13, 2008.
U.S. Appl. No. 12/251,857, filed Oct. 15, 2008.
U.S. Appl. No. 12/253,457, filed Oct. 17, 2008.
U.S. Appl. No. 12/389,906, filed Feb. 20, 2009.
U.S. Appl. No. 12/389,915, filed Feb. 20, 2009.
U.S. Appl. No. 12/401,268, filed Mar. 10, 2009.
U.S. Appl. No. 12/416,583, filed Apr. 1, 2009.
U.S. Appl. No. 12/419,395, filed Apr. 7, 2009.
U.S. Appl. No. 12/423,609, filed Apr. 14, 2009.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
U.S. Appl. No. 12/487,917, filed Jun. 19, 2009.
U.S. Appl. No. 12/493,302, filed Jun. 29, 2009.
U.S. Appl. No. 12/504,738, filed Jul. 17, 2009.
U.S. Appl. No. 12/535,851, filed Aug. 5, 2009.
U.S. Appl. No. 12/535,856, filed Aug. 5, 2009.
U.S. Appl. No. 12/536,616, filed Aug. 6, 2009.
U.S. Appl. No. 12/542,348, filed Aug. 17, 2009.
U.S. Appl. No. 12/542,785, filed Aug. 18, 2009.
U.S. Appl. No. 12/547,155, filed Aug. 25, 2009.
U.S. Appl. No. 12/548,644, filed Aug. 27, 2009.
U.S. Appl. No. 12/555,576, filed Sep. 8, 2009.
U.S. Appl. No. 12/556,010, filed Sep. 9, 2009.
U.S. Appl. No. 12/561,096, filed Sep. 16, 2009.
U.S. Appl. No. 12/562,575, filed Sep. 18, 2009.
U.S. Appl. No. 12/562,842, filed Sep. 18, 2009.
U.S. Appl. No. 12/566,299, filed Sep. 24, 2009.
U.S. Appl. No. 12/568,067, filed Sep. 28, 2009.
U.S. Appl. No. 12/568,524, filed Sep. 28, 2009.
U.S. Appl. No. 12/568,551, filed Sep. 28, 2009.
U.S. Appl. No. 12/568,777, filed Sep. 29, 2009.

(56) References Cited

OTHER PUBLICATIONS

U.S. Appl. No. 12/568,838, filed Sep. 29, 2009.
U.S. Appl. No. 12/568,883, filed Sep. 29, 2009.
U.S. Appl. No. 12/568,972, filed Sep. 29, 2009.
U.S. Appl. No. 12/569,171, filed Sep. 29, 2009.
U.S. Appl. No. 12/569,685, filed Sep. 29, 2009.
U.S. Appl. No. 12/582,857, filed Oct. 21, 2009.
U.S. Appl. No. 12/606,769, filed Oct. 27, 2009.
U.S. Appl. No. 12/607,221, filed Oct. 28, 2009.
U.S. Appl. No. 12/607,268, filed Oct. 28, 2009.
U.S. Appl. No. 12/619,462, filed Nov. 16, 2009.
U.S. Appl. No. 12/620,289, filed Nov. 17, 2009.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/ Wire Localizer, Namic ® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94 1n Biologic Effects of Nonionizing Electromagnetic Fields, CRC Press, Inc., pp. 1424-1428.

Chung et al., "Clinical Experience of Sutureless Closed Hemorrhoidectomy with LigaSure™" Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw•Hill, vol. 111, (1984), pp. 2490-2499.
Cosman et al., "Radiofrequency Lesion Generation and its Effect on Tissue Impedance", Applied Neurophysiology, 51:230-242, 1988.
Cosman et al., Theoretical Aspects of "Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Humphries Jr. et al., "Finite•Element Codes to Model Electrical Heating and Non•Llnear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure™ Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure™ Vessel Sealing System in Hemorrhoidectormy" American College of Surgeons (ACS) Clinic La Congress Poster (2000).
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.

(56) References Cited

OTHER PUBLICATIONS

LigaSure™ Vessel Sealing System, the Seal of Confidence in General, Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, pp. 205-210.
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817•825.
Urologix, Inc.—Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.

(56) References Cited

OTHER PUBLICATIONS

European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09166708 dated Oct. 15, 2009.
European Search Report EP 09169376.2 extended dated Dec. 16, 2009.
International Search Report PCT/US98/18640 dated Jan. 29, 1998.
International Search Report PCT/US98/23950 dated Jan. 14, 1998.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/USO4/15311 dated Jan. 12, 2004.
International Search Report PCT/US05/36168 dated Aug. 28, 2006.
International Search Report PCT/US08/052460 dated Apr. 24, 2008.
International Search Report PCT/US09/31658 dated Mar. 11, 2009.

* cited by examiner

_SYSTEM FOR MONITORING ABLATION SIZE_

BACKGROUND

1. Technical Field

The present disclosure relates to systems and methods that may be used in tissue ablation procedures. More particularly, the present disclosure relates to systems and methods for monitoring ablation size during tissue ablation procedures in real-time.

2. Background of Related Art

In the treatment of diseases such as cancer, certain types of cancer cells have been found to denature at elevated temperatures (which are slightly lower than temperatures normally injurious to healthy cells). These types of treatments, known generally as hyperthermia therapy, typically utilize electromagnetic radiation to heat diseased cells to temperatures above 41° C. while maintaining adjacent healthy cells at lower temperatures where irreversible cell destruction will not occur. Procedures utilizing electromagnetic radiation to heat tissue may include ablation of the tissue.

Microwave ablation procedures, e.g., such as those performed for menorrhagia, are typically done to ablate the targeted tissue to denature or kill the tissue. Many procedures and types of devices utilizing electromagnetic radiation therapy are known in the art. Such microwave therapy is typically used in the treatment of tissue and organs such as the prostate, heart, and liver.

One non-invasive procedure generally involves the treatment of tissue (e.g., a tumor) underlying the skin via the use of microwave energy. The microwave energy is able to non-invasively penetrate the skin to reach the underlying tissue. However, this non-invasive procedure may result in the unwanted heating of healthy tissue. Thus, the non-invasive use of microwave energy requires a great deal of control.

Currently, there are several types of systems and methods for monitoring ablation zone size. In certain instances, one or more types of sensors (or other suitable devices) are operably associated with the microwave ablation device. For example, in a microwave ablation device that includes a monopole antenna configuration, an elongated microwave conductor may be in operative communication with a sensor exposed at an end of the microwave conductor. This type of sensor is sometimes surrounded by a dielectric sleeve.

Typically, the foregoing types of sensors are configured to function (e.g., provide feedback to a controller for controlling the power output of a power source) when the microwave ablation device is inactive, i.e., not radiating. That is, the foregoing sensors do not function in real-time. Typically, the power source is powered off or pulsed off when the sensors are providing feedback (e.g., tissue temperature) to the controller and/or other device(s) configured to control the power source.

SUMMARY

The present disclosure provides a system for monitoring ablation size in real-time. The system includes a power source. A microwave antenna is configured to deliver microwave energy from the power source to tissue to form an ablation zone. A plurality of spaced-apart electrodes is operably disposed along a length of the microwave antenna. The electrodes are disposed in electrical communication with one another. Each of the electrodes has a threshold impedance associated therewith corresponding to the radius of the ablation zone.

The present disclosure provides a microwave antenna adapted to connect to a power source configured for performing an ablation procedure. The microwave antenna includes a radiating section configured to deliver microwave energy from the power source to tissue to form an ablation zone. The microwave antenna includes a plurality of spaced-apart electrodes operably disposed along a length of the microwave antenna. The electrodes are disposed in electrical communication with one another. Each of the electrodes has a threshold impedance associated therewith corresponding to the radius of the ablation zone.

The present disclosure also provides a method for monitoring tissue undergoing ablation. The method includes the initial step of transmitting microwave energy from a power source to a microwave antenna to form a tissue ablation zone. A step of the method includes monitoring one or more electrodes impedance along the microwave antenna as the tissue ablation zone forms. Triggering a detection signal when a predetermined electrode impedance is reached at the at least one electrode along the microwave antenna is another step of the method. The method includes adjusting the amount of microwave energy from the power source to the microwave antenna.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
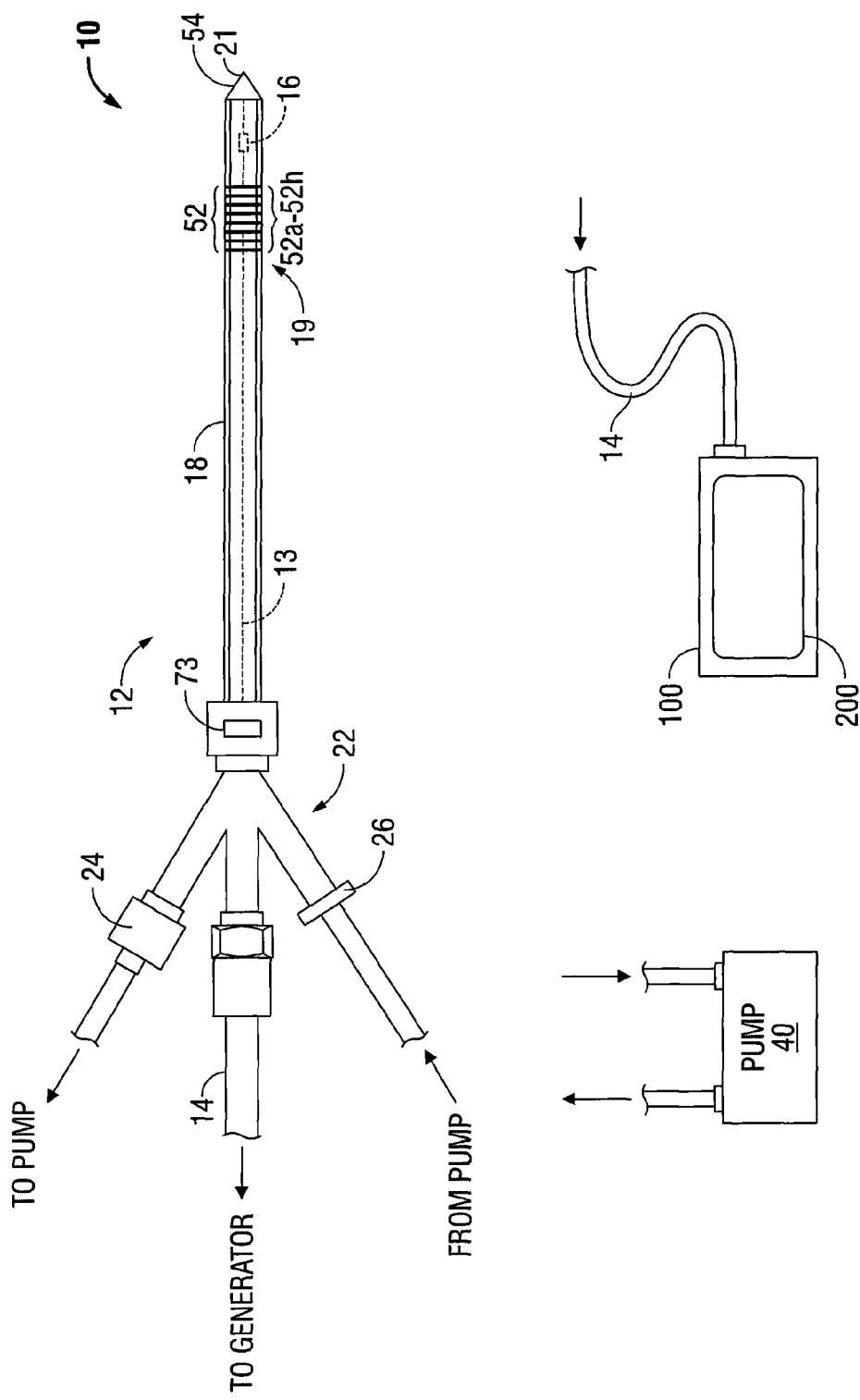
FIG. 1 is a perspective view of a system for monitoring ablation size according to an embodiment of the present disclosure.

Embodiments of the presently disclosed system and method are described in detail with reference to the drawing figures wherein like reference numerals identify similar or identical elements. As used herein and as is traditional, the term "distal" refers to the portion which is furthest from the user and the term "proximal" refers to the portion that is closest to the user. In addition, terms such as "above", "below", "forward", "rearward", etc. refer to the orientation of the figures or the direction of components and are simply used for convenience of description.

Figure 2:
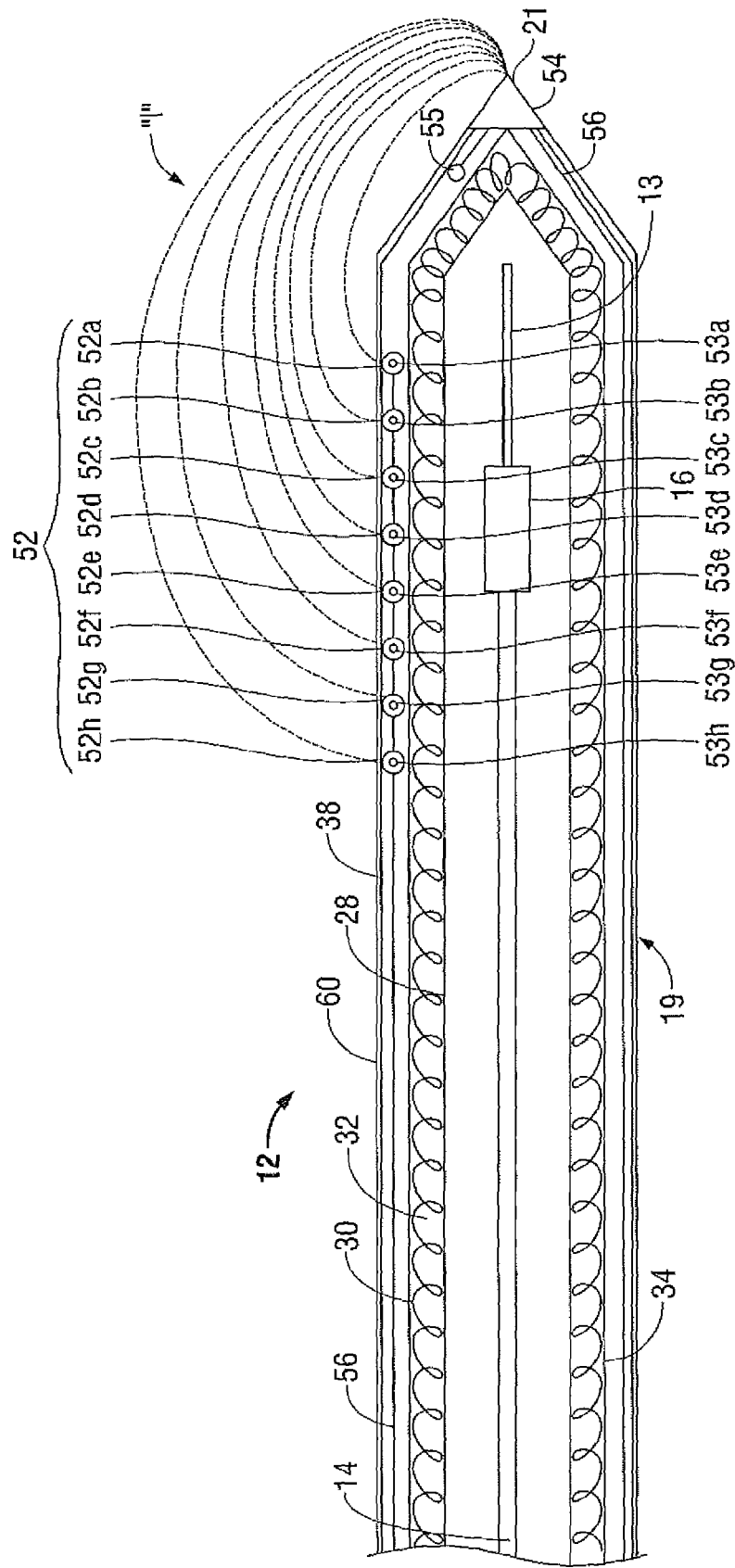
FIG. 2 is partial, side view illustrating internal components of a distal tip of a microwave antenna depicted in FIG. 1.

Referring now to FIGS. 1 and 2, and initially with reference to FIG. 1, a system for monitoring ablation size in accordance with an embodiment of the present disclosure is designated 10. A microwave antenna 12 operably couples to generator 100 and includes a controller 200 that connects to the generator 100 via a flexible coaxial cable 14. In this instance, generator 100 is configured to provide microwave energy at an operational frequency from about 500 MHz to about 10 GHz. Microwave antenna 12 includes a radiating section or portion 16 (FIGS. 1 and 2) that is connected by a feedline or shaft 18 to coaxial cable 14 and extends from the proximal end of the microwave antenna 12. Cable 14 includes an inner conductor 13 that is operably disposed within the shaft 18 and in electrical communication with a radiating section 16 (FIGS. 1 and 2). Microwave antenna 12 couples to the cable 14 through a connection hub 22. The connection hub 22 includes an outlet fluid port 24 and an inlet fluid port 26 connected in fluid communication with a sheath or cannula 28 (FIG. 2). Cannula 28 is configured to circulate coolant fluid 30 from ports 24 and 26 around the antenna assembly 12 via respective fluid lumens 32 and 34 (FIG. 2). Ports 24 and 26, in turn, couple to a supply pump 40. For a more detailed description of the microwave antenna 12 and operative components associated therewith, reference is made to commonly-owned U.S. patent application Ser. No. 12/401,268 filed on Mar. 10, 2009.

With continued reference to FIGS. 1 and 2, two or more spaced-apart electrodes 52 and 54 are operably disposed along a length of the shaft 18. More particularly, the electrodes 52 and 54 are disposed in proximity to a distal end 19 of the shaft 18. In the embodiment illustrated in FIG. 2, electrodes 52 include a series of proximal spaced-apart electrodes 52a-52h and a distal electrode 54. As defined herein, a series of electrodes is meant to mean two or more electrodes. For purposes herein, the series of proximal spaced-apart electrodes 52a-52h referred to proximal electrodes 52. The configuration of the electrodes 52 and 54 enables physical space sampling of an ablation site. More particularly, in one particular embodiment, during the delivery of microwave energy to the microwave antenna 12, impedance between one or more of the proximal electrodes 52, e.g., proximal electrode 52a, and the distal electrode 54 is measured and compared with known impedance values associated with the microwave antenna 12 and/or proximal electrodes 52, e.g., proximal electrode 52a. The configuration of each proximal electrodes 52a-52h and distal electrode 54 provides a separate closed loop path for current to flow, i.e., an electrical circuit, when the microwave antenna 12 is inserted into tissue at a target tissue site. Impedance is measured between each proximal electrode 52a-52h and the distal electrode 54, as described in greater detail below.

Proximal electrodes 52a-52h may be formed from any suitable conductive or partially conductive material. For example, proximal electrodes 52-52h may be formed from copper, silver, gold, etc. Proximal electrodes 52a-52h are operably positioned along an outer peripheral surface 38 of the shaft 18 in a manner suitable for the intended purposes described herein. In embodiments, the proximal electrodes 52a-52h may extend circumferentially along the outer peripheral surface 38 or partially along a length of the shaft 18. In the illustrative embodiment, proximal electrodes 52a-52h extend partially along the outer peripheral surface 38 in a linear manner forming a generally linear array along the outer peripheral surface 38 of the shaft 18. Proximal electrodes 52a-52h may be secured to the outer peripheral surface 38 and/or the shaft 18 via any suitable method(s). In one particular embodiment, the proximal electrodes 52a-52h are secured to the outer peripheral surface 38 via an epoxy adhesive (or other suitable adhesive). Proximal electrodes 52a-52h are in operative communication with one or more modules, e.g., ablation zone control module 232 (AZCM), associated with the generator 100 and/or controller 200. To this end, a portion of the proximal electrodes 52a-52h connects to one or more electrical leads (not explicitly shown) that provide an electrical interface for the proximal electrodes 52a-52h and the AZCM 232. Moreover, the electrical leads provide an electrical interface that supplies current, i.e., from a current source (or other suitable device configured to generate current, voltage source, power source, etc.) to the proximal electrodes 52a-52h.

In certain embodiments, one or more sensors, e.g., sensors 53a-53h, may be in operative communication with a respective one or corresponding proximal electrode 52a-52h (as best seen in FIG. 2). In this instance, the sensors 53a-53h may be configured to provide real-time information pertaining to the proximal electrodes 52a-52h. More particularly, the sensors 53a-53h may be configured to provide real-time information pertaining to one or more electrical parameters (e.g., impedance, power, voltage, current, etc.) and/or other parameters associated with the proximal electrodes 52a-52h. More particularly, the sensors 53a-53h may be in the form of one or more types of thermal sensors such as, for example, a thermocouple, a thermistor, an optical fiber, etc. In one particular embodiment, the sensors 53a-53h are thermocouples 53a-53h.

Distal electrode 54 may be formed from any suitable conductive or partially conductive material, e.g., copper, silver, gold, etc. Distal electrode 54 may have any suitable configuration. For illustrative purposes, distal electrode 54 is shown operably disposed at a distal tip 21 of the shaft 18. In the illustrated embodiment, distal electrode 54 defines a conductive tissue piercing tip. In this instance, the distal electrode 54 facilitates insertion of the microwave antenna 12 into tissue at a target tissue site. Alternatively, distal electrode 54 may have a relatively blunt configuration. An electrical lead (not explicitly shown) provides an electrical interface for returning current from the distal electrode 54 back to the current source. In certain embodiments, distal electrode 54 may be in operative communication with one or more modules, e.g., AZCM 232, associated with the generator 100 and/or controller 200. In this instance, the electrical lead may provide an electrical interface for the distal electrode 54 and the AZCM 232.

In certain embodiments, one or more sensors, e.g., sensor 55, may be in operative communication with the distal electrodes 54 (see FIG. 2, for example) and may provide information relevant to the proper operation of distal electrode 54 to the AZCM 232. Sensor 55 may be any suitable type of sensor such as, for example, one or more types of thermal sensors previously described above, e.g., a thermocouple.

A dielectric sheath 60 having a suitable thickness and made from a suitable material is operably positioned along a length of the microwave antenna 12 and substantially encases the proximal electrodes 52a-52h and distal electrode 54 in a manner that allows current to flow from the proximal electrodes 52a-52h to the distal electrode 54. Dielectric sheath 60 may be made from any suitable material and may be affixed to the microwave antenna 12 by any suitable affixing methods. In the illustrated embodiment, the dielectric sheath 60 is a vapor deposited dielectric material, such as, for example, parylene, that is applied to the microwave antenna 12. Substantially encasing the microwave antenna 12 with dielectric sheath 60 results in capacitive impedance that can allow RF current flow to/from the electrodes 52a-52h and tissue. More particularly, during transmission of microwave energy from the generator 100 to the microwave antenna 12 and when the proximal electrodes 52a-52h and distal electrode 54 are positioned within tissue adjacent a target tissue site, current flows from proximal electrodes 52a-52h to the electrode 54. Dielectric sheath 60 is configured to focus current densities "I" at the proximal electrodes 52a-52h and/or the distal electrode 54, which, in turn, provides comprehensive and/or more accurate measurements of impedance at the proximal electrode 52a-52h, as best seen in FIG. 2. In certain embodiments, the dielectric sheath 60 may fully encase the proximal electrodes 52a-52h and distal electrode 54. In this instance, the dielectric sheath 60 includes a thickness that allows current to pass from the proximal electrodes 52a-52h through the dielectric sheath 60 and to the distal electrode 54. In one particular embodiment, the thickness of the dielectric material of the dielectric sheath 60 ranges from about 0.0001 inches to about 0.001 inches.

As mentioned above, proximal electrodes 52a-52h (and in some instances distal electrode 54) is in operative communication with the generator 100 including AZCM 232 and/or controller 200. More particularly, the proximal electrodes 52a-52h and distal electrode 54 couple to the generator 100 and/or controller 200 via one or more suitable conductive mediums (e.g., a wire or cable 56) that extends from proximal electrodes 52a-52h and distal electrode 54 to the proximal end of the microwave antenna 12 and connects to the generator 100 (see FIG. 2, for example). In the illustrated embodiment, wire 56 is operably disposed within cable 14. Wire 56 electrically connects to the proximal electrodes 52a-52h and distal electrode 54 via the one or more leads previously described. The configuration of wire 56, proximal electrodes 52a-52h and distal electrode 54 forms a closed loop current path when the electrodes 52 and distal electrode 54 are positioned within tissue adjacent a target tissue site. In the illustrated embodiment, the wire 56 extends along the outer peripheral surface 38 of the shaft 18 and is encased by the dielectric sheath 60. Alternatively, the wire 56 may extend within and along a length of the shaft 18.

Figure 3:
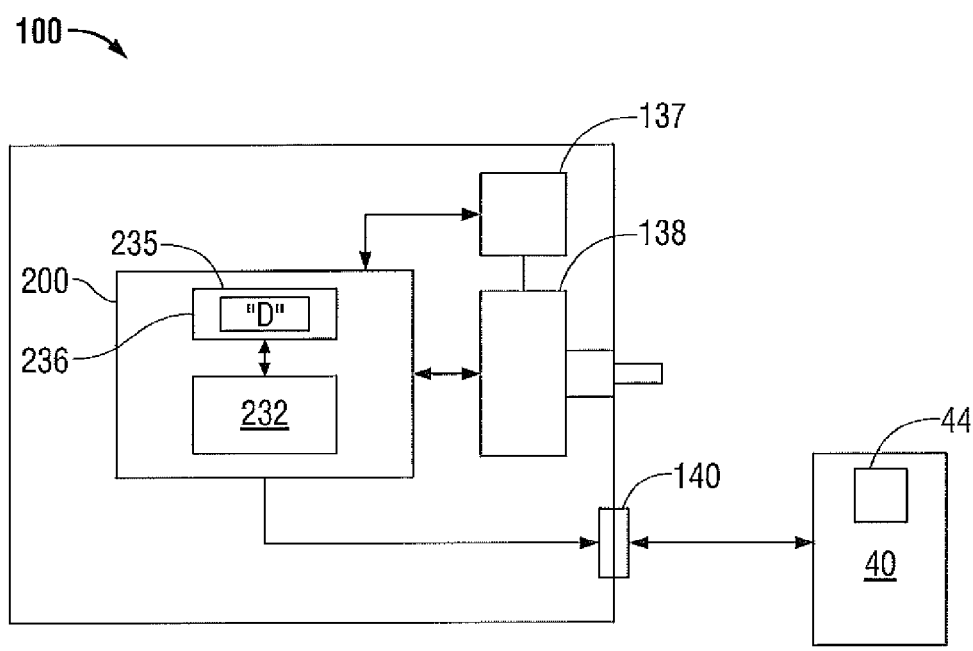
FIG. 3 is a functional block diagram showing a power source for use with the system depicted in FIG. 1.

With reference to FIG. 3, a schematic black diagram of the generator 100 is illustrated. The generator 100 includes a controller 200 including one or more modules (e.g., an AZCM 232), a power supply 137, a microwave output stage 138. In this instance, generator 100 is described with respect to the delivery of microwave energy. The power supply 137 provides DC power to the microwave output stage 138 which then converts the DC power into microwave energy and delivers the microwave energy to the radiating section 16 of the microwave antenna 12 (see FIG. 2). In the illustrated embodiment, a portion of the DC power is directed to the AZCM 232, described in greater detail below. The controller 200 may include analog and/or logic circuitry for processing sensed analog responses, e.g., impedance response, generated by the proximal electrodes 52a-52h and determining the control signals that are sent to the generator 100 and/or supply pump 40 via the microprocessor 235. More particularly, the controller 200 accepts one or more signals indicative of impedance associated with proximal electrodes 52a-52h adjacent an ablation zone and/or the microwave antenna 12, namely, the signals generated by the AZCM 232 as a result of the impedance measured and/or produced by proximal electrodes 52a-52h. One or more modules e.g., AZCM 232, of the controller 200 monitors and/or analyzes the impedance produced by the proximal electrodes 52a-52h and determines if a threshold impedance has been met. If the threshold impedance has been met, then the AZCM 232, microprocessor 235 and/or the controller 200 instructs the generator 100 to adjust the microwave output stage 138 and/or the power supply 137 accordingly. Additionally, the controller 200 may also signal the supply pump to adjust the amount of cooling fluid to the microwave antenna 12 and/or the surrounding tissue.

The controller 200 includes microprocessor 235 having memory 236 which may be volatile type memory (e.g., RAM) and/or non-volatile type memory (e.g., flash media, disk media, etc.). In the illustrated embodiment, the microprocessor 235 is in operative communication with the power supply 137 and/or microwave output stage 138 allowing the microprocessor 235 to control the output of the generator 100 according to either open and/or closed control loop schemes. The microprocessor 235 is capable of executing software instructions for processing data received by the AZCM 232, and for outputting control signals to the generator 100 and/or supply pump 40, accordingly. The software instructions, which are executable by the controller 200, are stored in the memory 236.

Figure 4A:
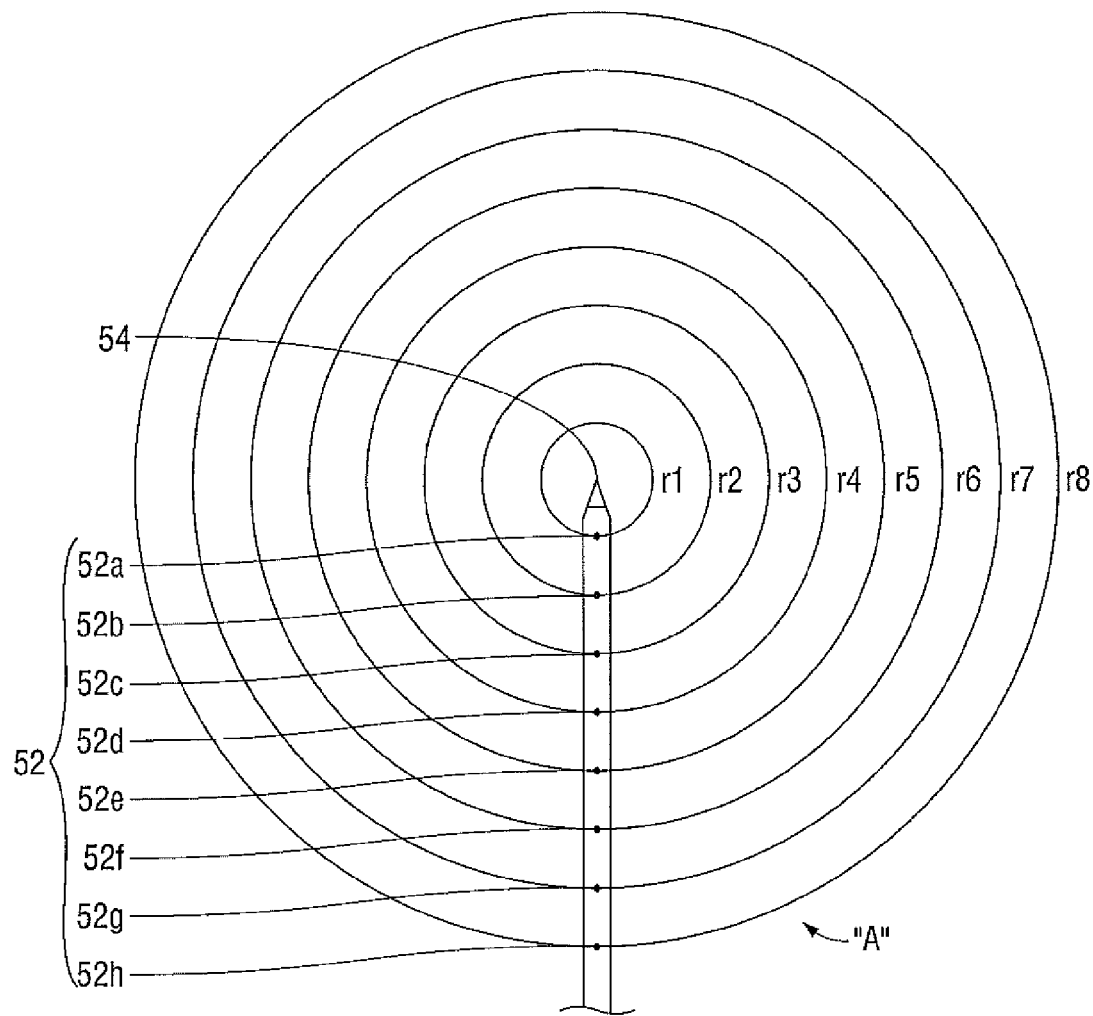
FIG. 4A is a schematic, plan view of a tip of the microwave antenna depicted in FIG. 2 illustrating radial ablation zones having a generally spherical configuration.
Figure 4B:
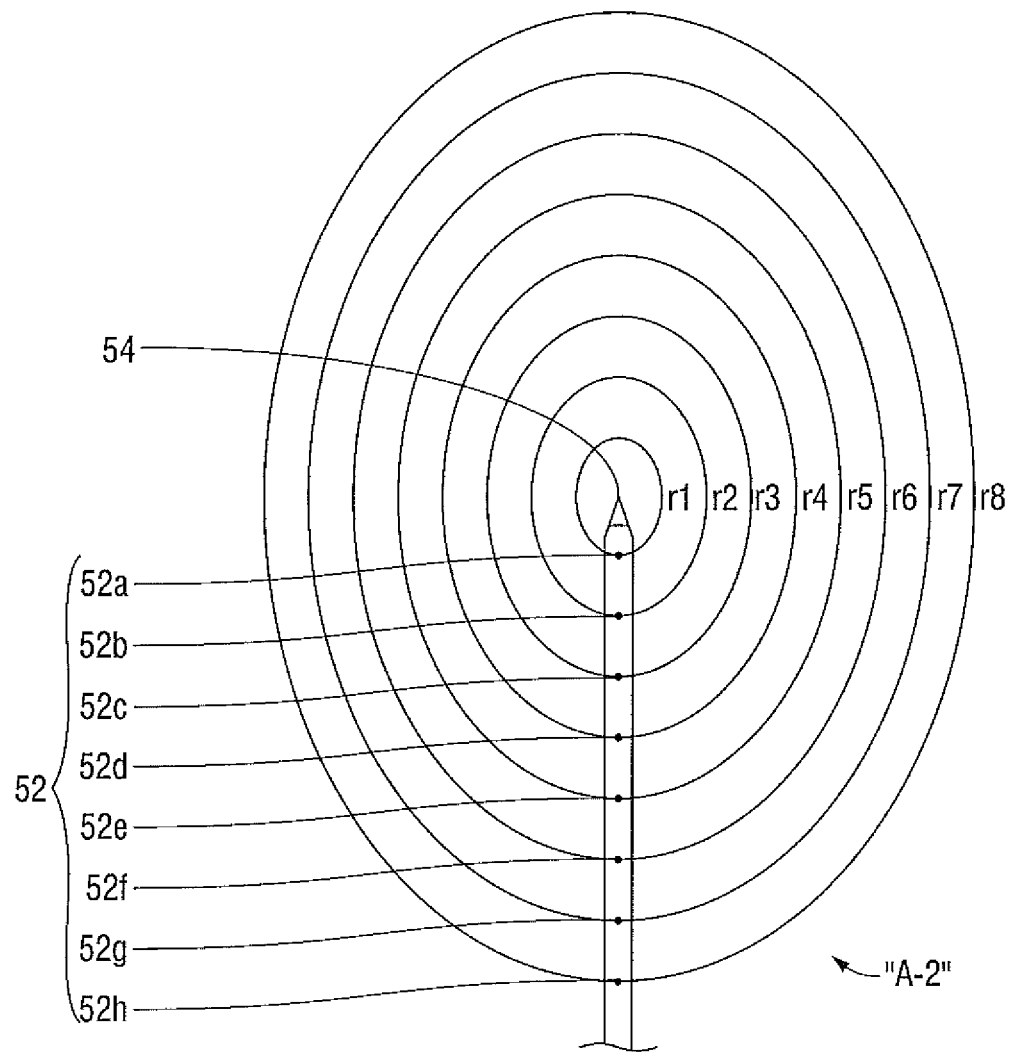
FIG. 4B is a schematic, plan view of a tip of the microwave antenna depicted in FIG. 2 illustrating radial ablation zones having a generally ellipsoidal configuration.

In accordance with the present disclosure, the microwave antenna 12 is configured to create an ablation zone "A" having any suitable configuration, such as, for example, spherical (FIG. 4A), hemispherical, ellipsoidal (FIG. 4B where the ablation zone is designated "A-2"), and so forth. In one particular embodiment, microwave antenna 12 is configured to create an ablation zone "A" that is spherical (FIG. 4A). To facilitate understanding of the present disclosure, ablation zone "A" is being defined having a plurality of concentric ablation zones having radii $r_1$-$r_8$ when measured from the center of the ablation zone "A," collectively referred to as radii r.

Figure 5A:
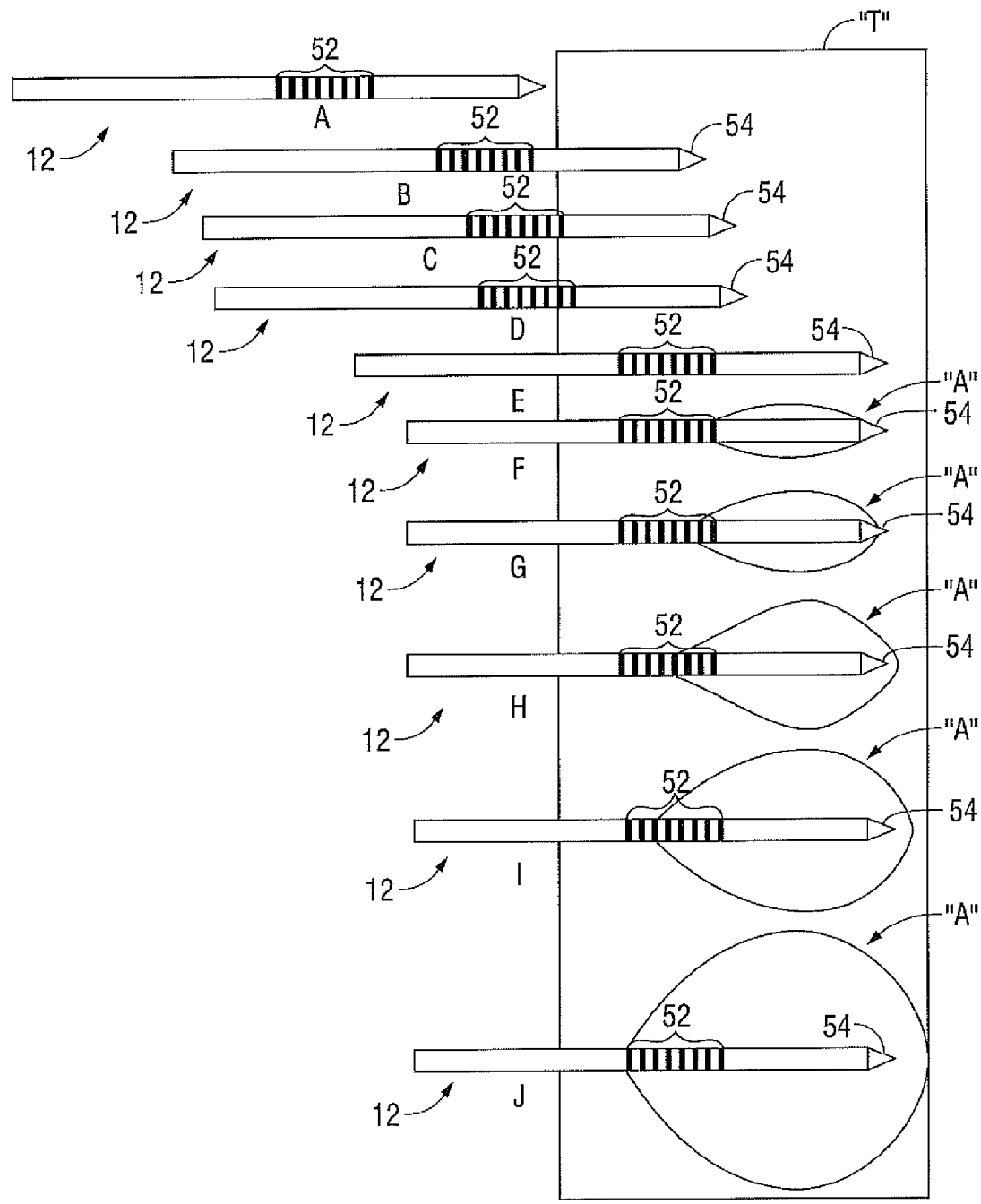
FIG. 5A is a schematic, plan view of a portion of the microwave antenna depicted in FIG. 1 showing a sequenced insertion of the microwave antenna into tissue.
Figure 5B:
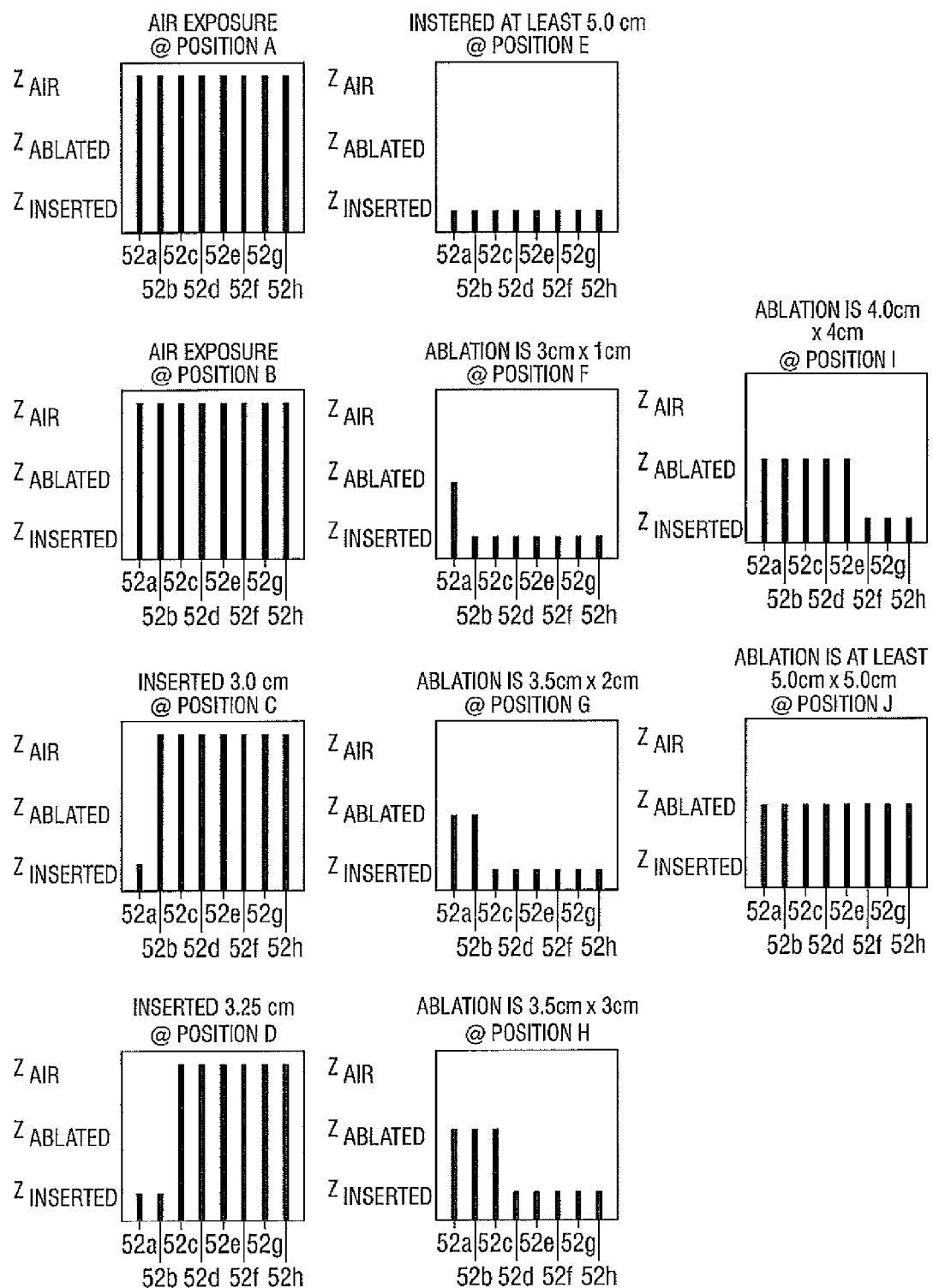
FIG. 5B is a graphical representation of corresponding impedances associated with respective electrodes of the microwave antenna depicted in FIG. 5A.
Figure 6:
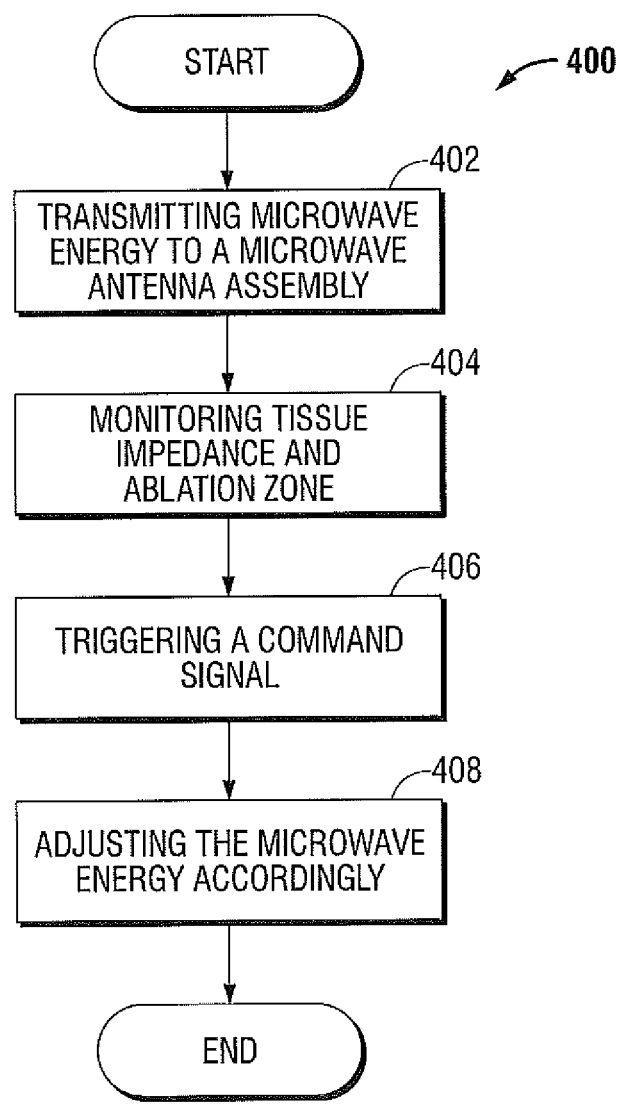
FIG. 6 is a flow chart illustrating a method for monitoring temperature of tissue undergoing ablation in accordance with the present disclosure.

With reference to FIGS. 5A and 5B, proximal electrodes 52a-52h in combination with distal electrode 54 are configured to provide comprehensive monitoring of an ablation zone "A" (FIGS. 4A and 5A at microwave position J). More particularly, the concept of the integration of impedance Z associated with proximal electrodes 52 over time may be used to indicate tissue damage, e.g., death or necrosis. For a given microwave antenna 12, each of the proximal electrodes 52a-52h has a predetermined threshold impedance Z associated therewith. The predetermined threshold impedance Z associated with a corresponding electrode 52a-52h, e.g., electrode 52a, and a corresponding radius "r," e.g., r1, may be determined via any suitable methods. For example, predetermined threshold impedances Z may be determined via known experimental test data, model equations, functions and graphs, or combination thereof.

In one particular embodiment, a control algorithm of the present disclosure uses known (or in certain instances predicted) threshold impedances Z at specific radii to create an ablation zone "A" having a radius "r." That is, impedances Z associated with proximal electrodes 52a-52h that correspond to specific radii are compiled into one or more look-up tables "D" and are stored in memory, e.g., memory 236, accessible by the microprocessor 235 and/or the AZCM 232 (FIG. 3). The AZCM 232 includes control circuitry that receives information from the proximal electrodes 52a-52h, and provides the information and the source of the information (e.g., the particular proximal electrode 52 providing the information) to the controller 200 and/or microprocessor 235. More particularly, AZCM 232 monitors the impedance Z at the proximal electrodes 52, e.g., proximal electrode 52a, and triggers a command signal in response to the proximal electrode 52a reaching a predetermined impedance Z such that the electrosurgical output power from the generator 100 may be adjusted (see FIG. 5A at microwave antenna 12 position F).

AZCM 232 may be configured to monitor impedance Z at the proximal electrodes 52a-52h by any known method(s). For example, in one particular embodiment, the AZCM 232 utilizes one or more equations (V=I×Z) to calculate the impedance at a particular electrode 52a-52h. In this instance, the voltage V and current I is known and the AZCM 232 calculates the impedance Z. Alternatively, or in combination therewith, the sensor(s) 53a-53h may provide thermal measurements at a respective electrode 52a-52h. With the impedance of a respective proximal electrode 52a-52h calculated and/or determined, AZCM 232, microprocessor 235 and/or controller 200 may access the one or more look-up tables "D" and confirm that the threshold impedance Z has been met and, subsequently, instruct the generator 100 to adjust the amount of microwave energy being delivered to the microwave antenna 12, see FIG. 5B at corresponding graphical representation F. This combination of events will provide an ablation zone "A" with a radius approximately equal to r3, i.e., an ablation zone approximately equal to 3 cm by 1 cm. It should be noted, that in this instance, the ablation zone "A" is more ellipsoidal than spherical. In embodiments, one or more control algorithms may utilize interpolation between the radii associated with the electrodes 52a-52h to calculate impedance between discreetly measured radii, e.g., impedance measured between electrode 52a and electrode 52b. More particularly, various (and commonly known) interpolation techniques may be utilized via curve fitting along the electrodes 52a-52h.

In certain instances, the one or more data look-up tables may be stored into memory during the manufacture process of the generator 100 and/or controller 200 or downloaded during programming; this is particularly useful in the instance where the generator 100 is configured for use with a single type of microwave antenna. Alternatively, the one or more data look-up tables may be downloaded into memory 236 at a time prior to use of the system 10; this is particularly useful in the instance where the generator 100 is configured for use with multiple microwave antennas that are configured to perform various ablation procedures.

In one particular embodiment, data look-up table "D" may be stored in a memory storage device 73 associated with the microwave antenna 12. More particularly, a data look-up table "D" may be stored in a memory storage device 73 operatively associated with the microwave antenna 12 and may be downloaded, read and stored into microprocessor 235 and/or memory 236 and, subsequently, accessed and utilized in a manner described above; this would dispose of the step of reprogramming the generator 100 and/or controller 200 for a specific microwave antenna. More particularly, the memory storage device 73 may be operably disposed on the microwave antenna 12, such as, for example, on or adjacent the hub 22 (FIG. 1). In this instance, when a user connects the microwave antenna 12 to the generator 100, the information contained in the memory storage device may be automatically read, downloaded and stored into the generator 100 and accessed for future use. The memory storage device 73 may also include information pertaining to the microwave antenna 12. Information, such as, for example, the type of microwave antenna, the type of tissue that the microwave antenna is configured to treat, the type of ablation zone desired, etc., may be stored into the storage device 73 associated with the microwave antenna 12.

In the embodiment illustrated in FIG. 1, the generator 100 is shown operably coupled to fluid supply pump 40. The supply pump 40 is, in turn, operably coupled to a supply tank 44. In embodiments, the microprocessor 235 is in operative communication with the supply pump 40 via one or more suitable types of interfaces, e.g., a port 140 operatively disposed on the generator 100, that allows the microprocessor 235 to control the output of a cooling fluid 30 from the supply pump 40 to the microwave antenna 12 according to either open and/or closed control loop schemes. The controller 200 may signal the supply pump 40 to control the output of cooling fluid 30 from the supply tank 44 to the microwave antenna 12. In this way, cooling fluid 30 is automatically circulated to the microwave antenna 12 and back to the supply pump 40. In certain embodiments, a clinician may manually control the supply pump 40 to cause cooling fluid 30 to be expelled from the microwave antenna 12 into and/or proximate the surrounding tissue.

Operation of system 10 is now described. For illustrative purposes, proximal electrodes 52a-52h may be considered as individual anodes and distal electrode 54 may be considered as a cathode. Each of the proximal electrodes 52a-52h includes a predetermined threshold impedance Z that has been previously determined by any of the aforementioned methods, e.g., experimental test data. Initially, microwave antenna 12 is connected to generator 100. In one particular embodiment, one or more modules, e.g., AZCM 232, associated with the generator 100 and/or controller 200 reads and/or downloads data, e.g., the type of microwave antenna, the type of tissue that is to be treated, data look-up tables, etc., from storage device 73 associated with the antenna 12. In the present example, the AZCM module 232 recognizes the microwave antenna 12 as having 8 proximal electrodes 52a-52h each with a predetermined threshold impedance Z that corresponds to a specific ablation zone "A." In one particular embodiment, the generator 100 prompts a user to enter the desired ablation zone size, e.g., ablation zone equal to 5 cm by 5 cm having a generally spherical configuration, see FIGS. 4A and 5A at microwave antenna 12 position J. After a user inputs the desired ablation zone size information, the AZCM 232 matches the desired ablation zone size with the particular electrode 52a-52h, e.g., proximal electrode 52h. The AZCM 232 sets the threshold impedance Z, e.g., Z ablated, for that particular proximal electrode. Thereafter, the generator 100 may be activated supplying microwave energy to the radiating section 16 of the microwave antenna 12 such that the tissue may be ablated.

AZCM 232 transmits DC current (or in some instances an RF signal, e.g., in the KHz or low MHz frequency spectrum) to each of the proximal electrodes 52a-52h. Prior to insertion of microwave antenna 12 into tissue "T", impedance Z associated with each of the plurality of proximal electrodes 52a-52h is relatively high, e.g., infinite; this is because an open circuit exists between the proximal electrodes 52a-52h and the distal electrode 54. Microwave antenna 12 including proximal electrodes 52a-52h may then be positioned within tissue (see FIGS. 5A and 5B at microwave antenna 12 position E and corresponding graph at position E, respectively) adjacent a target tissue site. Impedance Z associated with each of the plurality of proximal electrodes 52a-52h is relatively low, e.g., non-zero; this is because uncooked tissue has a finite or infinitesimal impedance. During tissue ablation, the AZCM 232 monitors impedance Z of the proximal electrodes 52a-52h. During tissue ablation, when a predetermined threshold impedance is reached (such as the impedance Z that corresponds to radius r8) at the particular proximal electrode 52a-52h, e.g., electrode 52h, and is detected by the AZCM 232, the AZCM 232 instructs the generator 100 to adjust the microwave energy accordingly. In the foregoing sequence of events, the proximal electrodes 52a-52h, distal electrode 54 and AZCM 232 function in real-time controlling the amount of microwave energy to the ablation zone such that a uniform ablation zone of suitable proportion is formed with minimal or no damage to adjacent tissue.

It should be noted that at any time during the ablation procedure, a user may adjust the previously inputted ablation zone size information. More particularly, if a user determines that during the course of the microwave ablation procedure the original ablation zone size needs to be adjusted, e.g., original ablation zone size is too big or too small, a user may simply input the new ablation zone size, and the AZCM 232 will adjust automatically. For example, if during the above example a user decides to adjust the ablation zone size to 4 cm by 4 cm (see FIGS. 5A and 5B at microwave antenna position D the AZCM 232 monitors proximal electrode 52*e* until proximal electrode 52*e* reaches the predetermined threshold impedance Z.

With reference to FIG. 5 a method 400 for monitoring tissue undergoing ablation is illustrated. At step 402, microwave energy from a generator 100 is transmitted to a microwave antenna 12 adjacent a tissue ablation site. At step, 404, one or more electrodes' impedance at the ablation site is monitored. At step 406, a detection signal is triggered when a predetermined electrode impedance is reached at the one or more electrodes along the microwave antenna. At step 408, the amount of microwave energy from the generator 200 to the microwave antenna may be adjusted.

From the foregoing and with reference to the various figure drawings, those skilled in the art will appreciate that certain modifications can also be made to the present disclosure without departing from the scope of the same. For example, the system 10 may be adapted to connect to an RF electrosurgical power source, e.g., an RF generator that includes or is in operative communication with one or more controllers 200 including an AZCM 232.

While the electrodes 52 have been described herein as including a series of proximal electrodes 52*a*-52*h* and a distal electrode 54 that is positioned at a distal tip 21 of the shaft 18, it is within the purview of the present disclosure that the distal electrode 54 may be positioned anywhere along the shaft 18, e.g., positioned adjacent the series of proximal electrodes 52*a*-52*h*. Or, in another embodiment, a distal electrode 54 may not be utilized. In this instance, one of the series of proximal electrodes 52*a*-52*h* may be configured to function in a manner as described above with respect to distal electrode 54.

Figure 7:
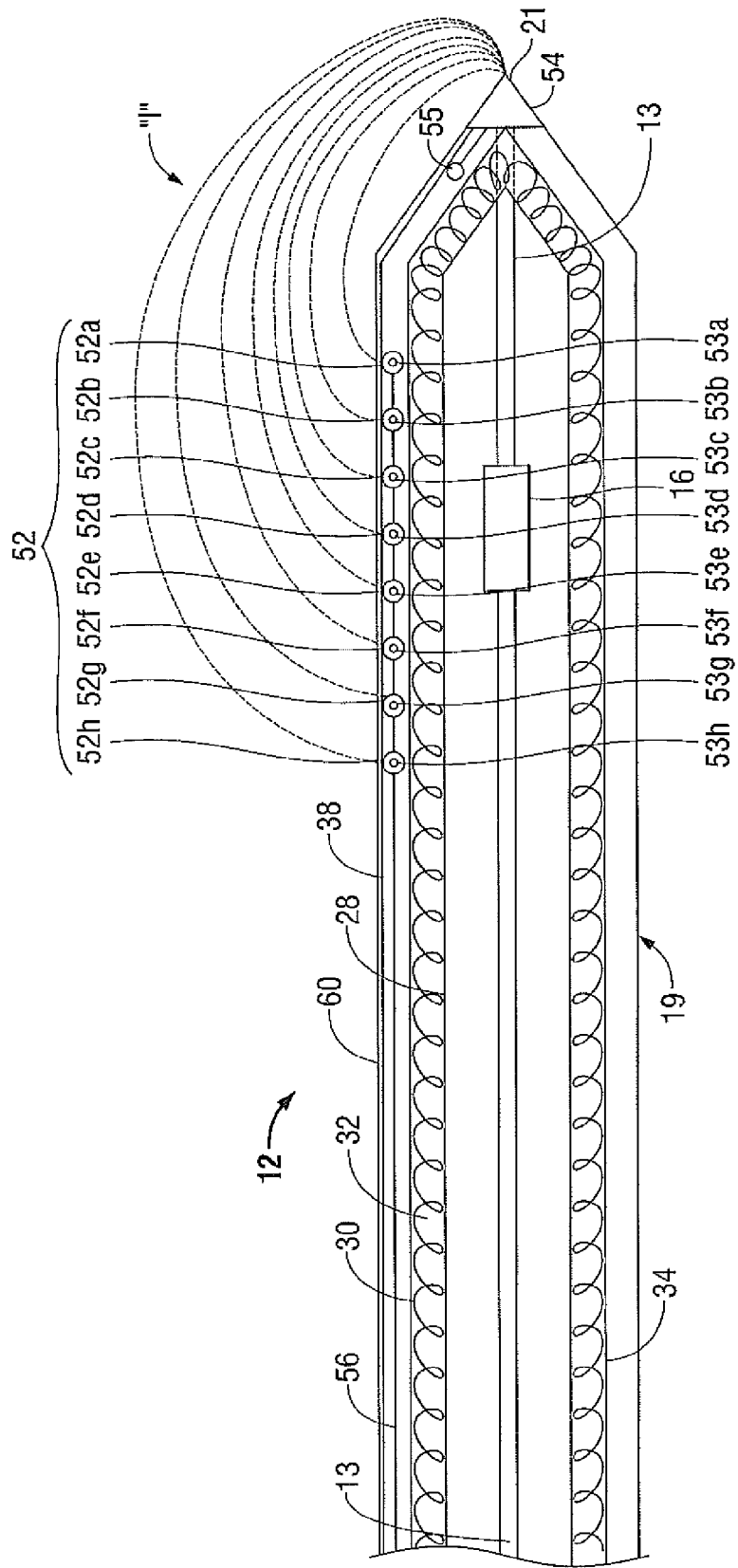
FIG. 7 is partial, side view illustrating internal components of a distal tip of a microwave antenna according to an alternate embodiment of the present disclosure.
Figure 8:
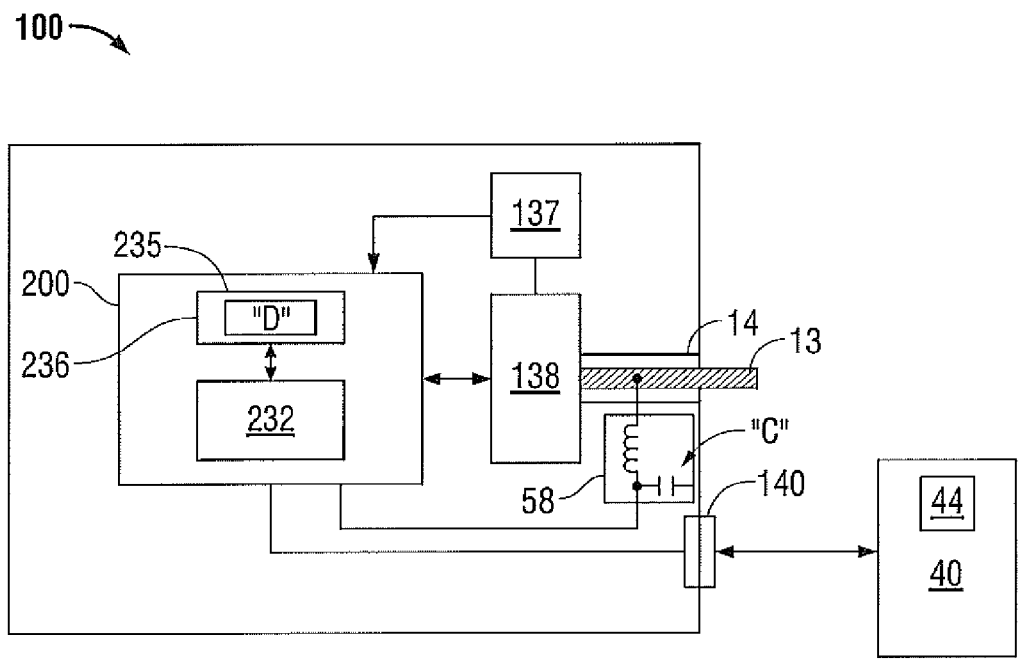
FIG. 8 is a functional block diagram showing a power source for use with the microwave antenna depicted in FIG. 7.

In certain embodiments, it may prove useful not to utilize a lead wire 56 that couples to distal electrode 54. In this instance, inner conductor 13 takes the place of the lead wire 56 and operably couples to the distal electrode 54, see FIG. 7, for example. More particularly, one or more types of DC blocks 58 are operatively associated with the microwave antenna 12. More particularly, DC block 58 is operably disposed within the generator 100 and in electrical communication with the inner conductor 13, shown schematically in FIG. 8. The DC block 58 prevents and/or limits direct current (DC) frequencies present at the distal electrode 54 from interfering with the microwave signals produced by the radiating section 16. DC block 58 may be configured in a manner that is conventional in the art. More particularly, DC block 58 may include one or more capacitors "C" configured in series with inner conductor 13 of the coaxial conductor 14, in series with an outer conductor (not explicitly shown) of the coaxial conductor 14, or in series with both the inner conductor 13 and outer conductor of the coaxial conductor 14. DC block 58 may be configured to function as a notch filter and designed to allow impedance measurement signals, i.e., impedance measurement signals that are in the KHz frequency range. In the embodiment illustrated in FIG. 7, lead wire 56 couples to the plurality of electrodes 52*a*-52*h* in a manner described above. Lead wire 56 is dimensioned to accommodate a respective RF signal that is transmitted to the distal electrode 54 and/or plurality of electrodes 52*a*-52*h* from the AZCM 232.

AZCM 232 is configured to transmit an RF impedance measurement signal to the proximal electrodes 52*a*-52*h* and/or the distal electrode 54. In the embodiment illustrated in FIG. 8, AZCM is configured to transmit an RF impedance measurement signal to the proximal electrodes 52*a*-52*h* and/or the distal electrode 54 that ranges from about 3 KHz to about 300 MHz.

Operation of system 10 that includes a generator 100 with a DC block 58 that is in operative communication with a microwave antenna 12 is substantially similar to that of a generator 100 without a DC block 58 and, as a result thereof, is not described herein.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A system for monitoring ablation size, comprising:
a power source having an electrical circuit that provides microwave energy;
a microwave antenna including a radiating section configured to deliver the microwave energy from the power source to tissue to form an ablation zone; and
a plurality of spaced-apart electrodes operably disposed along a length of the microwave antenna, the electrodes in electrical communication with one another, each of the electrodes having a threshold impedance associated therewith corresponding to the radius of the ablation zone,
wherein the plurality of spaced-apart electrodes includes a series of proximal spaced-apart electrodes along the shaft and a distal electrode operably disposed at a distal tip of the shaft, and
wherein a voltage potential is present between at least one of the series of proximal spaced-apart electrodes and the distal electrode as a result of delivery of microwave energy to the microwave antenna such that current flows between the at least one proximal electrode and the distal electrode and returns to the power source via a closed loop electrical circuit that is provided in the microwave antenna and separate from the electrical circuit that provides microwave energy to the radiating section of the microwave antenna.

2. A system according to claim 1, further including an ablation zone control module in operative communication with the microwave antenna and the power source and configured to instruct the power source to adjust the amount of microwave energy being delivered to the microwave antenna when a predetermined threshold impedance is generated by one of the electrodes to create a uniform ablation zone of suitable proportion with minimal damage to adjacent tissue.

3. A system according to claim 2, wherein the ablation zone control module and the plurality of spaced-apart electrodes are activated when the power source is activated.

4. A system according to claim 2, wherein at least one control algorithm operably associated with the ablation zone control module utilizes at least one data look-up table that includes information pertaining to predetermined threshold impedance values associated with the plurality of spaced-apart electrodes and corresponding radii.

5. A system according to claim 4, wherein the information pertaining to predetermined threshold impedance values associated with the plurality of spaced-apart electrodes and corresponding radii is pre-programmed into the power source and accessible by one of the ablation zone control module and a microprocessor.

6. A system according to claim 4, wherein the information pertaining to predetermined threshold impedance values associated with the plurality of spaced-apart electrodes and corresponding radii is stored on the microwave antenna and downloaded into a memory of the power source and accessible by one of the ablation zone control module and a microprocessor.

7. A system according to claim 1, wherein the plurality of spaced-apart electrodes is operably positioned on a portion of a shaft associated with the microwave antenna.

8. A system according to claim 1, wherein a wire connects to each of the series of proximal spaced-apart electrodes and the distal electrode.

9. A system according to claim 1, wherein a dielectric sheathing is operably positioned along a length of the microwave antenna and encases the series of proximally spaced-apart electrodes in a manner that allows current to flow between the series of proximally spaced-apart electrodes and the distal electrode.

10. A system according to claim 1, wherein the microwave antenna is configured to produce an ablation zone that is one of spherical and ellipsoidal.

11. A system according to claim 1, further comprising:
    at least one fluid pump configured to supply a cooling fluid to the microwave antenna for facilitating cooling of one of the microwave antenna and tissue adjacent the ablation zone.

12. A microwave antenna adapted to connect to a power source configured for performing an ablation procedure, comprising:
    a radiating section configured to deliver microwave energy from a power source to tissue to form an ablation zone, the power source having an electrical circuit that provides the microwave energy to the radiating section; and
    a plurality of spaced-apart electrodes operably disposed along a length of the microwave antenna, the plurality of spaced-apart electrodes disposed in electrical communication with one another, each of the plurality of spaced-apart electrodes having a threshold impedance associated therewith corresponding to the radius of the ablation zone,
    wherein the plurality of spaced-apart electrodes includes a series of proximal spaced-apart electrodes along the shaft and a distal electrode operably disposed at a distal tip of the shaft, and
    wherein a voltage potential is present between at least one of the series of proximal spaced-apart electrodes and the distal electrode as a result of delivery of microwave energy to the microwave antenna such that current flows between the at least one proximal electrode and the distal electrode and returns to the power source via a closed loop electrical circuit that is provided in the microwave antenna and separate from the electrical circuit that provides the microwave energy to the radiating section of the microwave antenna.

13. A microwave antenna according to claim 12, wherein the plurality of spaced-apart electrodes are operably positioned on a portion of a shaft associated with the microwave antenna.

14. A microwave antenna according to claim 12, wherein a wire connects each of the series of proximal spaced-apart electrodes and the distal electrode.

15. A system according to claim 14, wherein a dielectric sheathing is operably positioned along a length of the microwave antenna and encases the series of proximally spaced-apart electrodes in a manner that allows current to flow between the series of proximally spaced-apart electrodes and the distal electrode.

* * * * *